(12) United States Patent
Li

(10) Patent No.: US 7,288,084 B2
(45) Date of Patent: Oct. 30, 2007

(54) DRUG-LOADED MEDICAL DEVICE

(75) Inventor: Jianmin Li, Lexington, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 177 days.

(21) Appl. No.: 10/424,621

(22) Filed: Apr. 28, 2003

(65) Prior Publication Data

US 2004/0215169 A1 Oct. 28, 2004

(51) Int. Cl.
*A61K 9/22* (2006.01)
(52) U.S. Cl. .............................. 604/890.1; 604/891.1; 623/1.42; 424/424
(58) Field of Classification Search .............. 604/537, 604/265, 890.1–892.1, 48, 500, 502, 507, 604/508, 57, 93.01, 103.01, 523–527, 285, 604/288, 544; 424/422–426, 430; 623/1.42–1.48, 623/23.64, 23.66, 23.7; 600/6, 12, 11
See application file for complete search history.

(56) References Cited

U.S. PATENT DOCUMENTS

| | | | |
|---|---|---|---|
| 4,314,556 A * | 2/1982 | Ma | 604/187 |
| 5,372,600 A | 12/1994 | Beyar et al. | |
| 5,554,147 A | 9/1996 | Batich et al. | |
| 5,607,417 A | 3/1997 | Batich et al. | |
| 5,629,008 A | 5/1997 | Lee | |
| 5,709,667 A * | 1/1998 | Carilli | 604/198 |
| 5,788,687 A | 8/1998 | Batich et al. | |
| 5,843,172 A | 12/1998 | Yan | |
| 5,985,307 A | 11/1999 | Hanson et al. | |
| 6,071,305 A * | 6/2000 | Brown et al. | 623/1.43 |
| 6,280,411 B1 | 8/2001 | Lennox | |
| 6,299,597 B1 | 10/2001 | Buscemi et al. | |
| 6,306,422 B1 | 10/2001 | Batich et al. | |
| 6,316,018 B1 | 11/2001 | Ding et al. | |
| 6,827,737 B2 * | 12/2004 | Hill et al. | 623/1.4 |
| 2001/0007931 A1 * | 7/2001 | Blatter | 604/103.01 |
| 2001/0029660 A1 | 10/2001 | Johnson | |
| 2001/0041883 A1 * | 11/2001 | Devonec | 604/544 |
| 2002/0082679 A1 | 6/2002 | Sirhan et al. | |
| 2002/0090388 A1 | 7/2002 | Humes et al. | |
| 2004/0230156 A1 * | 11/2004 | Schreck et al. | 604/96.01 |

FOREIGN PATENT DOCUMENTS

| | | |
|---|---|---|
| DE | 10150995 A1 | 4/2003 |
| WO | WO93/05730 | 4/1993 |
| WO | WO98/34669 | 8/1998 |
| WO | WO 02/078778 A1 | 10/2002 |

\* cited by examiner

*Primary Examiner*—Catherine S. Williams
(74) *Attorney, Agent, or Firm*—Mayer & Williams PC; Keum J. Park, Esq.

(57) ABSTRACT

A medical device is designed to be placed in a patient's body and release one or more therapeutic agents therefrom. The medical device includes an elongated member defining a passage for passing bodily fluids therethrough and at least one enclosed internal space for containing one or more therapeutic agents therein. The elongated member may further define one or more pores in fluid communication with the enclosed internal space. The medical device can deliver one or more therapeutic agents at a desired level or volume, over a desired period of time, and from a desired location of the device. Therapeutic agents may be released through the body of the medical device by diffusion and/or through the one or more pores.

41 Claims, 7 Drawing Sheets

DRUG-LOADED MEDICAL DEVICE

TECHNICAL FIELD

This invention generally relates to drug releasing medical devices.

BACKGROUND INFORMATION

A drug or therapeutic agent can be delivered to a patient by a medical device, such as, for example, a stent. Stents have been employed, for example, in the urethra, the ureters, the biliary tract, the cervix, the rectum, the esophagus, and blood vessels to relieve the pathological effects of constrictions occurring in these passageways.

Generally, drug-loaded stents are manufactured by blending the therapeutic agent with a polymer before forming the device or, alternatively, imbibing a drug into an existing medical device. The drawbacks of these methods are that the processing conditions may affect the stability of the therapeutic agent and/or the properties of the polymer and the finished devices. Blending the therapeutic agent with a polymer usually requires heating the mixture to temperatures that can negatively affect the therapeutic efficacy and/or the stability of the agent. Additionally, imbibing techniques usually employ a solvent for dissolving the therapeutic agent. Solvents, however, can be incompatible with some therapeutic agents and may compromise the solubility and/or therapeutic efficacy of the agent. Also, solvents can be incompatible with the polymer and affect certain properties of the medical device, such as, for example, rigidity or other mechanical properties.

SUMMARY OF THE INVENTION

The invention relates to a device placed in the patient's body for passing bodily fluids and delivering one or more therapeutic agents to the body of a patient. A stent, according to the invention can be manufactured using a biocompatible polymer and can include a passage for passing the bodily fluids and at least one enclosed internal space. One or more therapeutic agents are loaded into the at least one enclosed internal space (for example, after the stent is formed) and are consequently not subjected to any detrimental effects of high temperatures and/or solvents. Stents according to the present invention can be manufactured using various polymers and drugs.

A stent of the present invention can deliver one or more therapeutic agents at a desired level, over a desired period of time, and from a desired location of the device. One or more therapeutic agents can be released into the patient by diffusing through the body of the stent and/or through pores that lead into the enclosed internal space. The level of drug delivery can be controlled by the chemical properties of the polymer used to manufacture the stent (e.g., polymers that permit or prevent diffusion therethrough) and the size and number of pores leading into the enclosed internal space. The timing of release of the therapeutic agent may be controlled by plugging the pores with a biodegradable material having a predetermined degradation rate and/or disposing a biodegradable coating around the elongated member. The polymer used to manufacture the stent and/or the location of the pores can control the location where drug-release occurs and the dosing.

In one aspect, the invention is directed to a medical device for passing one or more bodily fluids and releasing at least one therapeutic agent into a body of a patient. The medical device includes an elongated member defining a passage for passing the one or more bodily fluids, the passage extending at least partially through the elongated member, and an enclosed internal space defined as a reservoir within the elongated member for holding at least one therapeutic agent.

In one embodiment of the foregoing aspect of the invention, the therapeutic agent is placeable within at least a portion of the enclosed internal space and is releasable into the body of the patient through a portion of the surface or along the entire surface of the elongated member when the medical device is disposed within the body of the patient. In various embodiments of the foregoing aspect of the invention, the elongated member defines at least one pore in communication with the enclosed internal space for releasing the at least one therapeutic agent into the body of the patient, when the medical device is disposed within the body of the patient. In another embodiment, the medical device further includes at least one plug disposed within at least one pore. The at least one plug can be a biodegradable barrier. In yet another embodiment, the elongated member includes a hydrophobic polymer. The elongated member can also define at least one sealed opening at one end of the elongated member, wherein the opening is in communication with the enclosed internal space to provide access to the enclosed internal space for loading the at least one therapeutic agent prior to use. The opening may be sealed with a radiopaque material or sealed by a biodegradable material. Also, the enclosed internal space can extend along substantially the entire length of the elongated member.

In some embodiments of the foregoing aspect of the invention, the passage is eccentric to the elongated member. In other embodiments, the enclosed internal space extends along a length of the elongated member substantially parallel to the passage. In a further embodiment, the enclosed internal space is eccentric to the elongated member. The medical device may further include a biodegradable coating disposed on an external surface of the elongated member, and the biodegradable coating may include at least one therapeutic agent. In another embodiment, the elongated member includes a first polymer having a first durometer value and a second polymer having a second durometer value.

In various embodiments of the foregoing aspect of the invention, the medical device further includes a second enclosed internal space defined as a reservoir within the elongated member for holding a second therapeutic agent. The enclosed internal space and second enclosed internal space can be disposed on opposite sides of the passage along the longitudinal axis of the elongated member. In some embodiments, the medical device further includes a second therapeutic agent placeable within at least a portion of the second enclosed internal space and releasable into the body of the patient through the elongated member when the medical device is disposed within the body of the patient. The at least one therapeutic agent and the second therapeutic agent may be the same. The first and second therapeutic agents may be disposed in the same enclosed internal space in the device. The enclosed internal space or second enclosed internal space can include a plurality of therapeutic agents. In one embodiment, the elongated member defines at least one pore in communication with the second enclosed internal space for releasing the second therapeutic agent into the body of the patient, when the medical device is disposed within the body of the patient. In another embodiment, the medical device further includes at least one plug disposed within the at least one pore. The at least one plug can be a biodegradable barrier.

In another aspect, the invention relates to a method of placing a medical device for passing one or more bodily fluids and releasing at least one therapeutic agent into a body of a patient. The method includes the step of providing a medical device that includes an elongated member defining a passage for passing the one or more bodily fluids, the passage extending at least partially through the elongated member, and an enclosed internal space defined by the elongated member for holding the at least one therapeutic agent. The method further includes the step of placing the medical device into the body of the patient. In one embodiment, the at least one therapeutic agent is placeable within at least a portion of the enclosed internal space and is releasable into the body of the patient through the elongated member when the medical device is disposed within the body of the patient.

In various embodiments of the foregoing aspect of the invention, the elongated member also defines an opening at one end of the elongated member, wherein the opening is in communication with the enclosed internal space to provide access to the enclosed internal space for loading the at least one therapeutic agent. The opening is sealed after loading the agent and prior to the medical device being disposed within the body of the patient. In other embodiments, the opening is sealed with a radiopaque material or sealed by a biodegradable material. In a further embodiment, the placing step includes viewing the radiopaque material through a fluoroscope.

In yet another aspect, the invention relates to a method for delivering at least one therapeutic agent into a body of a patient. The method includes the steps of providing a medical device, placing the medical device within the body of the patient, and passing the at least one therapeutic agent through the elongated member, thereby delivering the therapeutic agent to the body of the patient. The medical device includes an elongated member defining a passage for passing one or more bodily fluids, wherein the passage extends at least partially through the elongated member, and an enclosed internal space defined by the elongated member for holding the at least one therapeutic agent. The medical device further includes at least one therapeutic agent placeable within at least a portion of the enclosed internal space. The at least one therapeutic agent is releasable into the body of the patient through the elongated member when the medical device is disposed within the body of the patient. In one embodiment, the placing step includes inserting the medical device within a urethra and/or ureter. In another embodiment, the at least one therapeutic agent is passed through the elongated member by diffusion and/or dissolution.

In further embodiments of the foregoing aspect of the invention, the elongated member defines at least one pore in communication with the enclosed internal space for releasing the at least one therapeutic agent into the body of the patient, when the medical device is disposed within the body of the patient. In one embodiment, the passing step includes passing the at least one therapeutic agent through the at least one pore. In some embodiments, the medical device further includes at least one plug disposed within the at least one pore. The at least one plug can be a biodegradable barrier. In another embodiment, the passing step includes degrading the biodegradable barrier and passing the at least one therapeutic agent through the at least one pore. In still another embodiment, the elongated member includes a hydrophobic polymer.

In various embodiments of the foregoing aspect of the invention, the medical device includes a biodegradable coating disposed on an external surface of the elongated member. The biodegradable coating may include a therapeutic agent. In one embodiment, the passing step includes releasing the therapeutic agent by degrading the biodegradable coating into the body of the patient.

These and other objects, along with advantages and features of the present invention, will become apparent through reference to the following description, the accompanying drawings, and the claims. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same parts throughout the different views. Also, the drawings are not necessarily to scale, emphasis generally being placed upon illustrating the principles of the invention. In the following description, various embodiments of the present invention are described with reference to the following drawings, in which.

DESCRIPTION

Embodiments of the present invention are described below. The invention is not limited, however, to these embodiments. For example, various embodiments of the invention are described in terms of a urethral stent and a ureteral stent; however, embodiments of the invention may be used in one or more other lumens within a body.

In accordance with the invention, a medical device, such as, for example, a stent for use in the urinary system of a mammal can be a vehicle to deliver one or more therapeutic agents to the body of the mammal. A stent of the present invention includes an elongated member defining a passage and an enclosed internal space for holding a therapeutic agent therein. A wide variety of polymer and therapeutic agent combinations may be used to manufacture the drug-loaded stent, as the invention circumvents the detrimental effects that accompany the use of solvents and exposing the agent(s) to high processing temperatures. In addition, by using certain polymers and/or including pores in the stent, the level, time, duration, and location of release of the therapeutic agent can be controlled.

Figure 1:
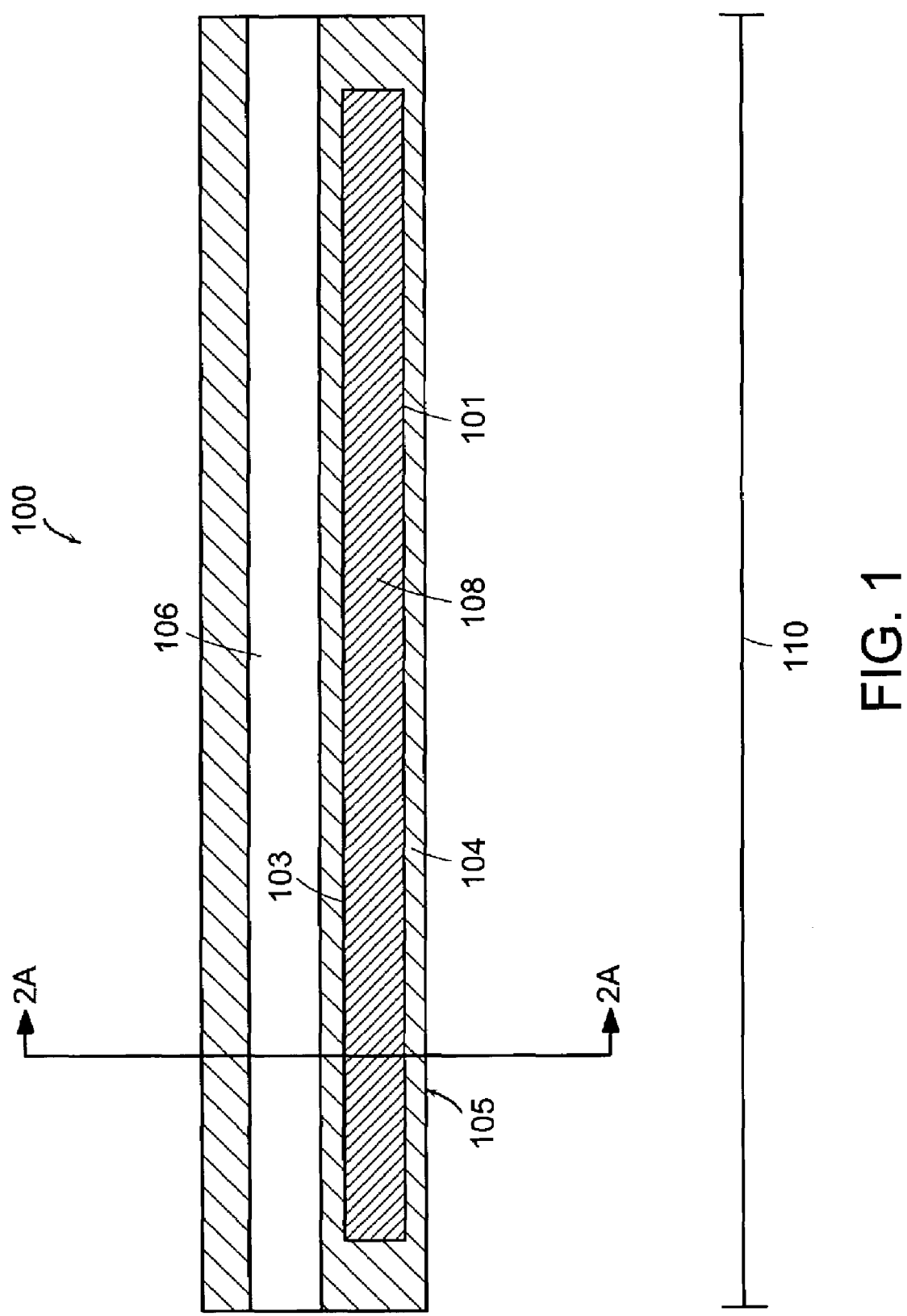
FIG. 1 is a schematic longitudinal cross-section of an embodiment of a stent in accordance with the invention.

FIG. 1 shows a longitudinal cross-section of a stent 100 in accordance with the invention. The stent 100 includes an elongated member 110 that defines a passage 106 extending therethrough. The elongated member 110 further defines an enclosed internal space 101 adjacent to the passage 106. The enclosed internal space 101 is shown with a therapeutic agent 108 disposed therein. The therapeutic agent 108 contained within the enclosed internal space 101 may be in various forms, such as a liquid, gel, or a solid. The elongated member 110 further includes walls 103, 104 positioned on opposite sides of the enclosed internal space 101. Wall 103 is disposed between the enclosed internal space 101 and the passage 106. Wall 104 is disposed adjacent to an outer surface 105 of the stent 100. In operation, the stent 100 maintains a flow of bodily fluids through the passage 106 and releases the therapeutic agent 108 into the patient's body by various mechanisms, such as diffusing through the walls 103, 104 of the stent 100.

Figure 2C:
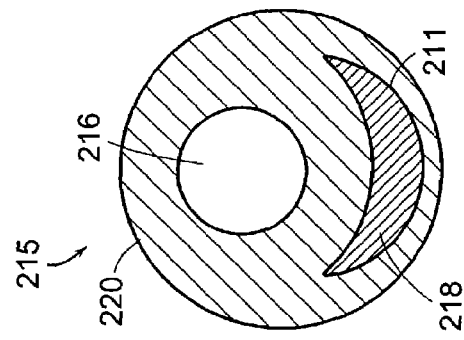
FIGS. 2B-2E are schematic transverse cross-sectional views of alternative embodiments of a stent in accordance with the invention.
Figure 2B:
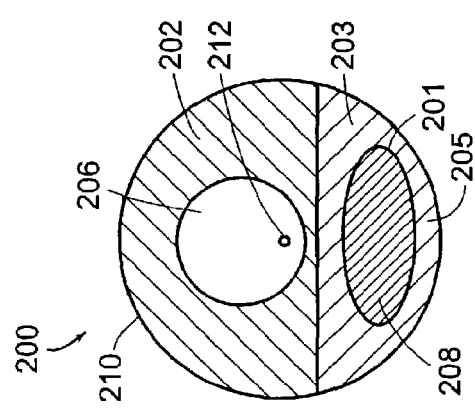
Figure 2A:
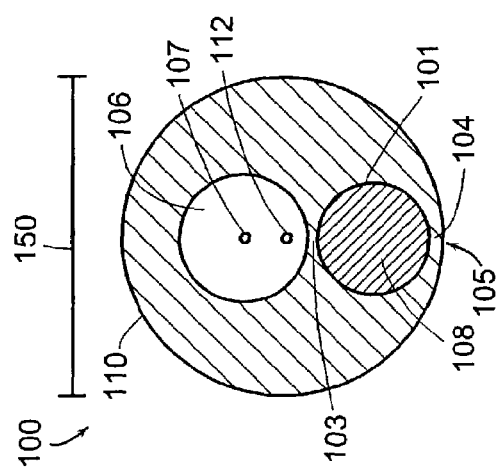
FIG. 2A is a schematic transverse cross-sectional view of the stent of FIG. 1 taken at line 2A-2A.

FIG. 2A is a cross-section of the stent 100 of FIG. 1 taken at line 2A-2A. To maximize the volume of the enclosed internal space 101, the center axis 107 of the passage 106 is positioned off-center or eccentric relative to the center axis 112 of the elongated member 110, as shown in FIG. 2A. Furthermore, the enclosed internal space 101 is disposed adjacent to the passage 106 and is also positioned off-center relative to the center axis 107 of the elongated member 110. The off-centered arrangement of the passage 106 and the enclosed internal space 101 provides a greater drug-loading capacity, without having to increase an outside diameter 150 of the elongated member 110. FIG. 2A also shows the arrangement of the walls 103, 104. In particular, the cross-sectional view of stent 100 shows that portions of the elongated member 110 form the walls 103, 104. Although the passage 106 and the enclosed internal space 101 are depicted in a circular configuration, alternative cross-sectional configurations may be used, such as, for example, elliptical, polygonal, wedge-shaped, or combinations thereof.

FIGS. 2B-2E depict alternative cross-sectional views of a stent in accordance with the invention. FIG. 2B depicts a stent 200 with an enclosed internal space 201 having an elliptical cross-sectional shape and a passage 206 having a circular cross-sectional shape, both defined by an elongated member 210. The passage 206 is positioned off-center from a center axis 212 of the elongated member 210. In some cases, positioning the passage 206 and space 201 in off-centered arrangements alters the physical properties of the stent 200. For example, where the therapeutic agent 208 is a liquid, the radial strength of the elongated member 210 is reduced. Two factors contribute to the reduction in radial strength. First, disposing the enclosed internal space 201 in an off-centered position gives rise to a thin wall 205 that structurally weakens the elongated member 210. Second, when radial pressure is applied to the stent 200, the liquid within the enclosed internal space 201 may be unable to provide sufficient resistance to counter the radial pressure, thus collapsing the space 201. A reduced radial strength is often undesirable, as stents are generally employed to maintain an open passage through a bodily lumen by resisting radial pressure exerted by adjacent tissue.

In contrast, where the therapeutic agent 208 is a solid, the radial strength of the elongated member 210 is enhanced, because the solid within the enclosed internal space 201 supplies additional structural support to the stent 200. The enhanced radial strength provided by the solid therapeutic agent 208 can, however, render the stent 200 less flexible and, therefore, more difficult to insert into the patient's body.

To compensate for the change in physical properties of the stent 200 due to the off-centered position of the passage 206 and/or space 201, the elongated member 210 may include a first polymer 202 and a second polymer 203, wherein the polymers 202, 203 have different degrees of hardness on the Shore A durometer scale. For example, the first polymer 202 may be relatively hard and have a durometer value of about 80 to about 100 on a Shore A scale, preferably about 85 to about 95 on a Shore A scale, and more preferably about 90 on a Shore A scale. In contrast, the second polymer 203 may be relatively soft and have a durometer value of about 70 to about 90 on a Shore A scale, preferably about 78 to about 90 on a Shore A scale, and more preferably about 86 on a Shore A scale. The relative hardness of the polymers 202, 203 depends on the chemical state of the therapeutic agent and the desired property of the finished product. Specifically, where the therapeutic agent 208 in the enclosed internal space 201 is a liquid, the second polymer 203 has a greater hardness on the Shore A durometer scale than the first polymer 202. Conversely, if the therapeutic agent 208 is a solid, the second polymer 203 has a lower hardness on the Shore A durometer scale than the first polymer 202. Polymers of different hardness values may be used for different portions of the stent, along the length of the stent, such as in FIG. 2B, or used for different axial segments of the stent, such as distal, proximal and middle segments.

FIG. 2C depicts another alternative embodiment, wherein a stent 215 includes an elongated member 220 defining a circular passage 216 and a crescent-shaped enclosed internal space 211 with a therapeutic agent 218 disposed therein. In still another alternative embodiment, shown in FIG. 2D, a stent 225 includes an elongated member 230 that defines a passage 238, a first enclosed internal space 232, and a second enclosed internal space 231. A first therapeutic agent 228 and a second therapeutic agent 229 are disposed within the enclosed internal spaces 232 and 231, respectively. This embodiment allows the stent 225 to deliver two therapeutic agents to the patient's body from separate locations. In one embodiment, the therapeutic agents 228, 229 are identical. In some embodiments, the temporal release of the therapeutic agents is controlled, such that the agents 228, 229 are delivered simultaneously or in succession (See FIGS. 3 and 5). While both enclosed internal spaces 232, 231 are depicted in a circular configuration, alternative cross-sectional configurations may be used, such as, for example, elliptical, polygonal, wedge-shaped, or combinations thereof.

Figure 2E:
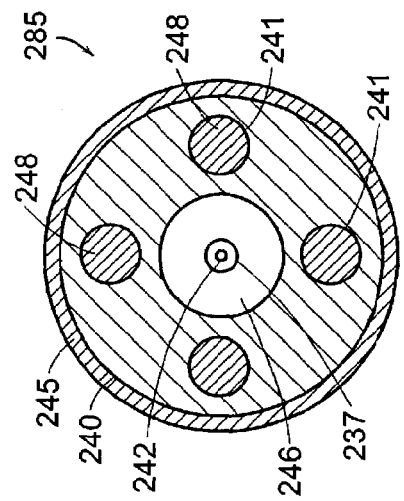
Figure 2D:
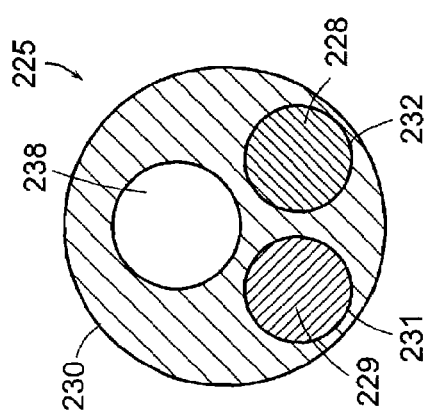

FIG. 2E depicts an alternative embodiment, wherein a stent 285 includes an elongated member 240 defining a passage 246 and a plurality of enclosed internal spaces 241 that contain a therapeutic agent 248 therein. Although the plurality of enclosed internal spaces 241 are shown containing a single therapeutic agent 248, each internal space 241 may contain at least one different agent. The center axis 237 of the passage 246 is coaxial with a center axis 242 of the elongated member 240. The plurality of enclosed internal spaces 241 are disposed about the passage 246 and may be spaced equally apart from one another, as shown in FIG. 2E. In an alternative embodiment, two or more of the enclosed internal spaces 241 may be disposed about the passage 246 in a clustered or grouped arrangement. In still another embodiment, the enclosed internal spaces 241 may be arranged in two distinct groups on opposite sides of the passage 246, wherein each group includes at least two enclosed internal spaces 241. While the plurality of enclosed internal spaces 241 are shown with circular cross-sectional configurations, alternative cross-sectional configurations may be used, such as, for example, elliptical, polygonal, wedge-shaped, or combinations thereof.

In an alternative embodiment of the present invention, the delivery of the therapeutic agent 248 may be delayed by disposing a biodegradable coating 245 around the elongated member 240, as shown, for example, in FIG. 2E. In operation, the coating 245 provides a distinct barrier to the therapeutic agent 248, thus delaying release and/or controlling the release rate of the therapeutic agent 248 to the patient. Once the coating 245 has degraded, the therapeutic agent 248 may be released from the elongated member 240 and diffused into the patient's body. In an alternative embodiment, the biodegradable coating 245 may also include a therapeutic agent.

Figure 3:
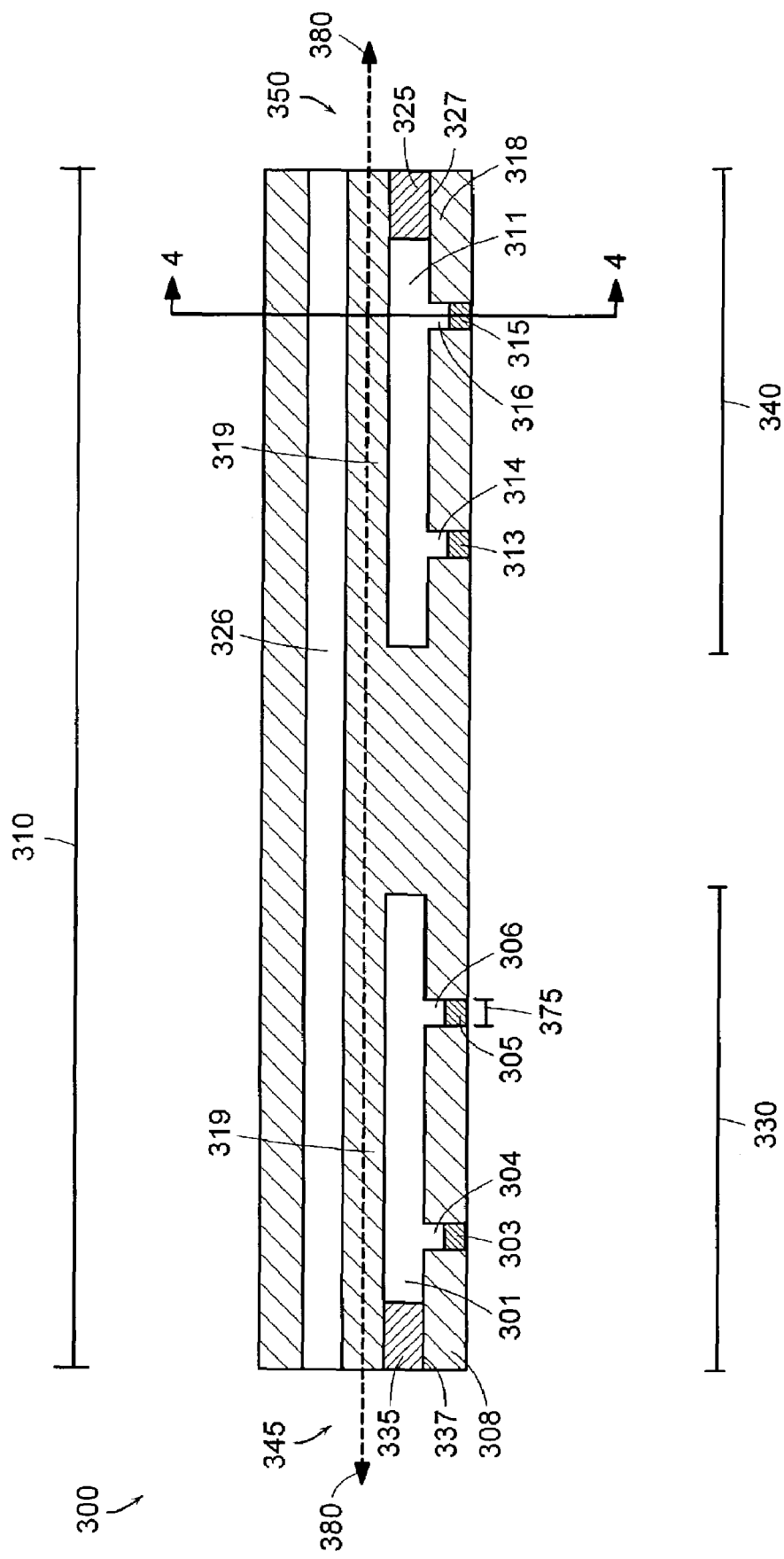
FIG. 3 is a schematic longitudinal cross-sectional view of an alternative embodiment of a stent in accordance with the invention.

FIG. 3 depicts a schematic cross-sectional view of an alternative embodiment of a stent 300 in accordance with the invention. The stent 300 includes an elongated member 310 defining a passage 326 extending therethrough. Further, the elongated member 310 defines a first enclosed internal space 301 and a second enclosed internal space 311. The enclosed internal spaces 301, 311 are arranged on substantially the same side of a longitudinal axis 380 of the elongated member 310, and may each contain a therapeutic agent. In one embodiment, the enclosed internal spaces 301, 311 contain different therapeutic agents.

The elongated member 310 depicted in FIG. 3 includes a first end 345, a second end 350 and a passage wall 319. The elongated member 310 further includes a first outer wall 308, and a second outer wall 318. A first insert 335 is disposed within a portion of the first enclosed internal space 301 and adjoins the first end 345 of the passage wall 319 and the first outer wall 308, thereby enclosing the first internal space 301. Together, the elongated member 310 and the first insert 335 define the first enclosed internal space 301. Also, a second insert 325 is disposed within a portion of the second enclosed internal space 311 and adjoins the second end 350 of the passage wall 319 and the second outer wall 318 to enclose the second internal space 311. The elongated member 310, together with the second insert 325, defines the second enclosed internal space 311. The inserts 335, 325 function to inhibit the one or more therapeutic agents contained in the enclosed internal spaces 301, 311 from escaping prior to the medical device being inserted into the body of the patient. The inserts 335, 325 may be constructed from biocompatible plastics and/or one or more biodegradable materials that degrade at a predetermined rate. Examples of these materials are provided hereinbelow.

The stent 300 may include at least one pore for releasing a therapeutic agent into the body of a patient. As shown in FIG. 3, the elongated member 310 defines a first pore 304 and a second pore 306. The pores 304, 306 are in fluid communication with the first enclosed internal space 301 to allow a therapeutic agent to pass therethrough. The elongated member 310 also defines a third pore 314 and a fourth pore 316 that are in fluid communication with the second enclosed internal space 311. Pores 314, 316 allow a therapeutic agent contained within the second enclosed internal space 311 to pass therethrough.

To control and/or delay the release of the therapeutic agent contained within the enclosed internal spaces 301, 311, the elongated member 310 may include a first plug 303, a second plug 305, a third plug 313 and a fourth plug 315. Specifically, the first plug 303 is disposed within the first pore 304 and the second plug 305 is disposed within the second pore 306. Likewise, the third plug 313 and fourth plug 315 are disposed within the third pore 314 and fourth pore 316, respectively. In one embodiment, the plugs 303, 305, 313, and 315 are constructed from one or more biodegradable materials that degrade at a predetermined rate.

Each plug may have its own degradation rate or the degradation rates can be the same. Biodegradable materials are described in greater detail hereinbelow.

Figure 4:
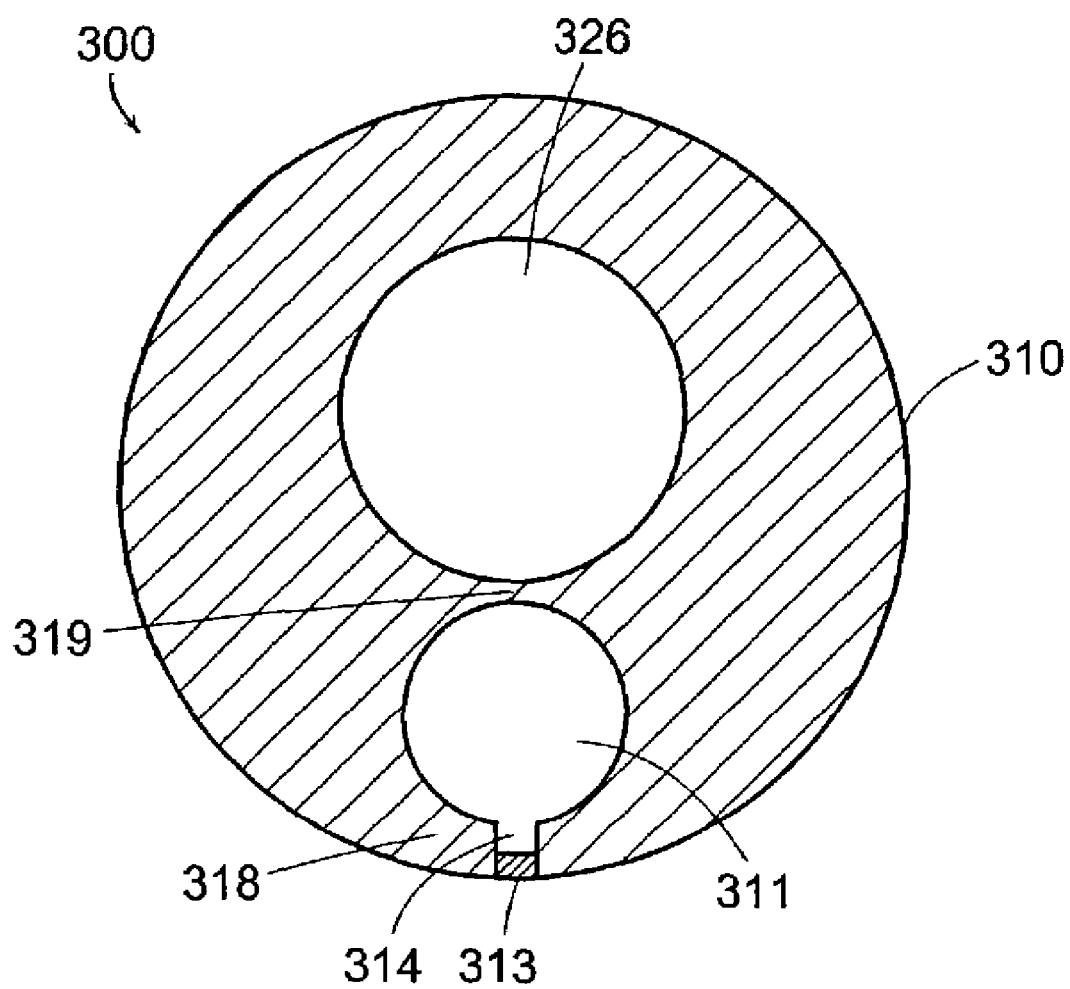
FIG. 4 is a schematic transverse cross-sectional view of the stent of FIG. 3 taken at line 4-4.

FIG. 4 is a an enlarged cross-sectional view taken at line 4-4 in FIG. 3. FIG. 4 shows the passage 326 and the third pore 314 in fluid communication with a portion of the second enclosed internal space 311. The biodegradable plug 313 is secured within the pore 314, so that the therapeutic agent is temporarily contained within the second enclosed internal space 311. FIG. 4 also shows the arrangement of the passage wall 319 and the second outer wall 318. That is, the cross-sectional view of stent 300 shows that the walls 319, 318 are formed by portions of the elongated member 310 and are disposed on opposite sides of enclosed internal space 311.

Biodegradable materials impervious to therapeutic agents may be used to control the timing of treatment. To control the release of the agent through the pores 304, 306, 314, 316, they may be occluded with biodegradable plugs 303, 305, 313, 315. In one embodiment, the plugs 303, 305, 313, 315 may degrade at different rates. For example, the first plug 303 and the third plug 313 may be manufactured such that they degrade at twice the rate of the second plug 305 and the fourth plug 315. As such, the dose-rate of the agents contained in the enclosed internal spaces 301, 311 increases two-fold over a predetermined period of time. Alternatively, the first plug 303 and the second plug 305 may degrade at twice the rate of the third plug 313 and the fourth plug 315. In that case, the elongated member 310 releases the agent contained in the first enclosed internal space 301 before releasing the agent contained in the second enclosed internal space 311.

Biodegradable components of the invention may be constructed from substances such as, but not limited to, collagen, alginates, carboxymethyl cellulose (CMC), polyhydroxybutyrate-polyhydroxyvalerate (PHBV), polylactic acid (PLA), polybutylene succinate (PBS), hydroxypropyl cellulose (HPC), dextrin, sugar, glucose, starch, and chelating agents, including ethylenediaminetetraacetic acid (EDTA), polyethylene glycol (PEG), and copolymers thereof.

In some embodiments, the pores do not need plugs. In such embodiments, the size of the pores can be used to control the slow release of therapeutic agents into the body of a patient. In other embodiments, the pores are only partially occluded by one or more biodegradable materials, thus allowing the release rate of the therapeutic agent to increase over time, once the medical device is inserted into the patient's body.

A variety of methods can be used to manufacture a medical device according to the invention. For example, extrusion or injection molding can be used. During extrusion, a molten state polymer is forced under high pressure through an opening, thus forming a medical device in the shape of the opening's cross-section. Initially, the solid polymer is melted by rotation of a screw and barrel under extreme heat, friction, and pressure. After the resulting molten polymer is forced through a pre-shaped die of desired cross-section, the extrudate is cooled either through immersion within a water bath or by exposure to air.

The medical device may be constructed from more than one polymer and may be manufactured using co-extrusion techniques commonly known in the art. For example, the stent 200 of FIG. 2B includes a first polymer 202 and a second polymer 203, wherein the polymers 202, 203 have different degrees of hardness on the Shore A durometer scale. In other embodiments, polymers 202, 203 may be hydrophobic and hydrophilic, respectively, thus controlling the diffusion profile of the stent 200. During the co-extrusion process, the molten state polymers 202, 203 are forced under pressure through an opening, simultaneously producing the elongated member 210 having heterogeneous physical and/or chemical properties.

Injection molding provides a similar mechanical method to manufacture the medical device of the present invention. During this process, an injection unit melts the polymer and subsequently injects the melt into a hollow mold cavity of desired shape. A ram-fed injection-molding machine contains a hydraulically operated plunger. The plunger spreads a thin layer polymer into a heated region, then converges the polymer melt at a nozzle, and lastly, injects the melt into the mold. Alternatively, a reciprocation screw injection molding machine utilizes a hydraulically operated rotating screw to melt, mix, and pump the polymer, after which, the screw serves as a plunger to inject the melt into the mold.

The medical device of the present invention may be constructed of a biocompatible plastic such as, but not limited to, any polyester, nylon based biocompatible polymers, polytetrafluoroethylene, silicone, polyurethane, polyethylene, and thermoplastics. In a particular embodiment, the medical device of the present invention is constructed from ethylene vinyl acetate (EVA).

Using the embodiment of FIG. 3 as an example, the stent 300 may be manufactured by extruding or injection molding an elongated member 310 with a passage 326 extending therethrough. Once the form is cooled, a laser drill may be used to bore the enclosed internal spaces 301, 311, and the pores 304, 306, 314, 316. The inside diameters or dimensions, the number, and the arrangement of the pores 304, 306, 314, 316 within the stent 300 may be varied to suit a particular application, for example, to control the location from where the therapeutic agent is delivered and/or the rate of flow of the therapeutic agent. The pores 304, 306, 314, 316 can be sealed with biodegradable plugs 303, 305, 313, 315, respectively, to delay the release of the therapeutic agent into the patient's body. In one embodiment, the plugs 303, 305, 313, 315 may be threaded and screwed into the pores 304, 306, 314, 316, respectively. In another embodiment, the plugs 303, 305, 313, 315 may be press fit into the pores 304, 306, 314, 316, respectively, such that the plugs 304, 306, 314, 316 sealingly engage the elongated member 310. Once the pores 304, 306, 314, 316 are sealed, one or more therapeutic agents may then be loaded into the enclosed internal spaces 301, 311 using various methods (as discussed in further detail below). The pores can also be left open for diffusion without the use of plugs.

The inserts 335, 325 are subsequently disposed within a portion of the enclosed internal spaces 301, 311 to contain the therapeutic agent therein. The first end 345 and the second end 350 of the elongated member 310 define openings 337 and 327, respectively, for receiving the inserts 335, 325. So that the physician can confirm by radiographic techniques the proper placement of the stent 300 in the patient's body, a small amount of metal or other radiopaque material, such as, for example, bismuth, may be embedded within the inserts 335, 325. Disposing the inserts 335, 325 in the elongated member 310 may be carried out by threading the inserts 335, 325 and screwing them into the openings 337, 327. In another embodiment, the inserts 335, 325 may be press fit into openings 337, 327, such that the inserts 335, 325 sealingly engage the elongated member 310. Furthermore, biocompatible adhesives or bonding techniques may be used to dispose the inserts 335, 325 into the elongated member 310.

Bonding the inserts 335, 325 to the elongated member may be performed by heat bonding techniques. Heat bonding functions by partially melting the plastic of a structure, allowing the melted plastic to adhere to a contacting surface or other component, and allowing the plastic to cool and harden, thus forming a bond. Heat bonding methods that include radio frequency bonding, induction heating, and conduction heating may be used. The plastic of a first component may be selected to melt at a similar temperature as a second component so that both components are melted during the heat bonding process. Alternatively, either the first or second component may be constructed from a plastic with a lower melting temperature than the other component in order that only the component with the lower melting temperature may melt during the bonding process.

Alternatively, the components may be bonded by the use of a solvent, such as cyclohexanone and/or methylethylketone. The solvent acts by dissolving and swelling the component materials. As the component materials dissolve and swell, the components adhere to each other. The solvent is then removed allowing for the dissolved and swollen materials to harden and thus complete the bonding process.

Figure 5:
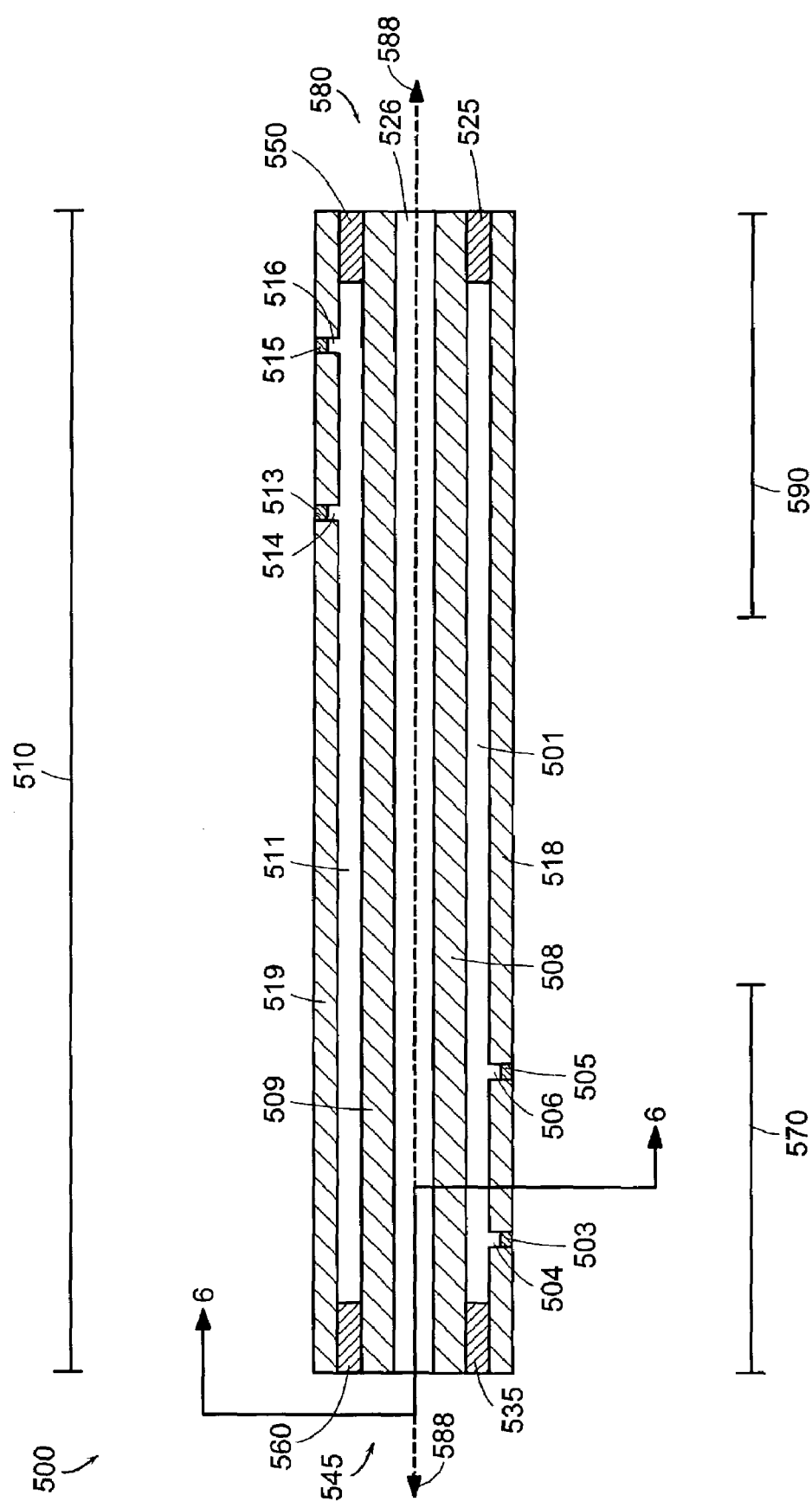
FIG. 5 is a schematic longitudinal cross-sectional view of an alternative embodiment of a stent in accordance with the invention.

FIG. 5 is a cross-sectional view of another alternative embodiment of a stent 500 in accordance with the invention. FIG. 5 shows an elongated member 510 with a first end 545, a second end 580, a first region 570, and a second region 590. The elongated member 510 defines a passage 526 extending therethrough, a first enclosed internal space 501, and a second enclosed internal space 511. The enclosed internal spaces 501, 511 are arranged on opposite sides of a longitudinal axis 588 of the elongated member 510. In one embodiment, the enclosed internal spaces 501, 511 contain one or more of the same or different therapeutic agents.

The elongated member 510 also includes a first outer wall 518, a second outer wall 519, a first passage wall 508, and a second passage wall 509. The stent 500 also includes a first insert 535 disposed within a portion of the first enclosed internal space 501 at the first end 545 of the elongated member 510. The first insert 535 adjoins a portion of the first passage wall 508 and a portion of the first outer wall 518 of the elongated member 510 to enclose the first enclosed internal space 501. Also, a second insert 525 is disposed within a portion of the first enclosed internal space 501 at the second end 580 of the elongated member. The second insert 525 adjoins a portion of the first passage wall 508 and a portion of the first outer wall 518 of the elongated member 510, thereby enclosing the first enclosed internal space 501. Together, the elongated member 510 and the inserts 535 and 525 define the first enclosed internal space 501.

In addition, a third insert 560 is disposed within a portion of the second enclosed internal space 511 at the first end 545 of the elongated member 510. The third insert 560 adjoins a portion of the second passage wall 509 and a portion of the second outer wall 519 of the elongated member 510 to enclose the second enclosed internal space 511. Similarly, a fourth insert 550 is disposed within a portion of the second enclosed internal space 511 at the second end 580 of the elongated member 510. The fourth insert 550 adjoins a portion of the second passage wall 509 and a portion of the second outer wall 519 of the elongated member 510, thus enclosing the second internal space 511. Together, the elongated member 510 and the inserts 560 and 550 define the second enclosed internal space 511. In an alternative embodiment, the stent 500 is manufactured such that the enclosed internal spaces 501, 511 extend only through a portion of the elongated member 510, thus employing only half the number of inserts for enclosing the internal spaces 501, 511.

The elongated member 510 also defines a first pore 504, a second pore 506, a third pore 514 and a fourth pore 516, which release the therapeutic agent(s) into the body of the patient. Pores 504, 506 are in fluid communication with the first enclosed space 501 in the first region 570 of the elongated member 510. Similarly, pores 514, 516 are in fluid communication with the second enclosed internal space 511 at the second region 590 of the elongated member 510. To control the release of the therapeutic agent contained within the enclosed internal spaces 511, 501, the elongated member 510 includes a first plug 503, a second plug 505, a third plug 513, and a fourth plug 515. Specifically, the first plug 503 is disposed within the first pore 504 and the second plug 505 is disposed within the second pore 506. Likewise, the third plug 513 and fourth plug 515 are disposed within the third pore 514 and fourth pore 516, respectively. In one embodiment the plugs 503, 505, 513, 515 are constructed from biodegradable materials that degrade at predetermined rates, which may be the same or different. The stent 500 may be manufactured using processes similar to those described hereinabove.

Figure 6:
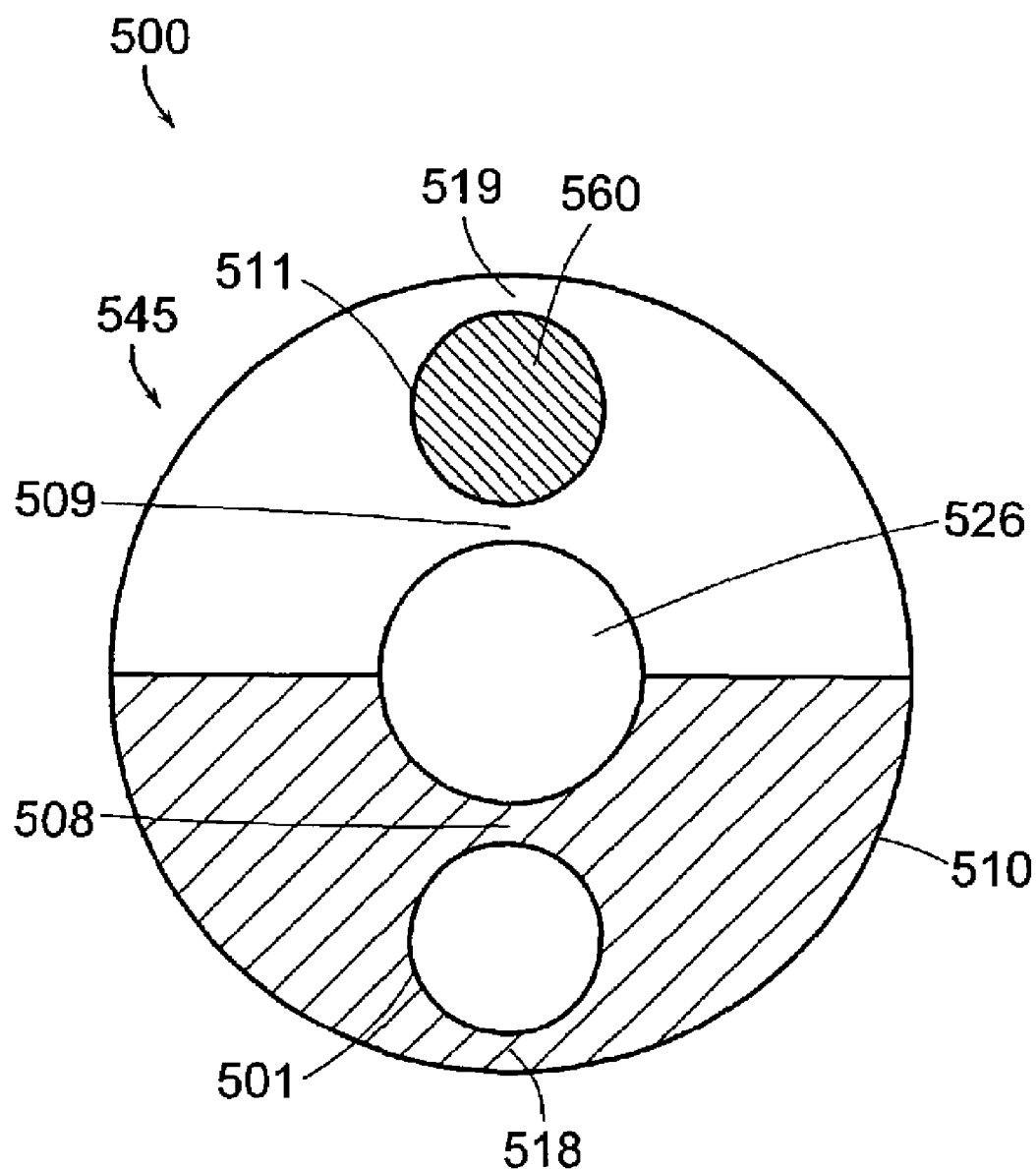
FIG. 6 is a schematic transverse cross-sectional view of the stent of FIG. 5 taken at line 6-6.

FIG. 6 is a an enlarged partial cross-sectional view taken at line 6-6 in FIG. 5. FIG. 6 shows the passage 526, the first enclosed internal space 501 and the third insert 560. The third insert 560 is disposed within the second enclosed internal space 511 at the first end 545 of the elongated member 510. FIG. 6 also shows the arrangement of the passage walls 508, 509 and the outer walls 518, 519. In particular, the cross-sectional view of stent 500 shows that the walls 508, 509, 518, 519 are formed by portions of the elongated member 510.

A therapeutic agent may be loaded into an enclosed internal space using various methods. Where the therapeutic agent is a liquid, a syringe may be used to inject the agent directly into the enclosed internal space. It is advantageous to seal one end of the enclosed internal space to prevent the liquid from escaping during the loading process. Where the therapeutic agent is a solid, such as, for example, a powder, the agent may be loaded into the enclosed internal space by gravity feeding or vacuum feeding. Using FIG. 5 as an example, vacuum feeding is carried out by coupling a vacuum to the first end 545 of the (unsealed) first enclosed internal space 501 with a filter disposed therebetween. The vacuum draws the therapeutic agent into the first enclosed internal space 501, which accumulates atop the filter and loads the first enclosed internal space 501.

In general, the therapeutic agent for use in connection with the present invention can be any pharmaceutically acceptable therapeutic agent. As used herein "pharmaceutically acceptable" means that an agent that is approved or capable of being approved by the United States Food and Drug Administration or Department of Agriculture for use in humans or animals when incorporated in or on an implantable or insertable medical device. Preferred therapeutic agents include anti-inflammatory agents, analgesic agents, local anesthetic agents, antispasmodic agents, and combinations thereof.

Anti-inflammatory agents include steroidal and non-steroidal anti-inflammatory agents. Examples of non-steroidal anti-inflammatory drugs, include aminoarylcarboxylic acid derivatives such as enfenamic acid, etofenamate, flufenamic acid, isonixin, meclofenamic acid, mefanamic acid, niflumic acid, talniflumate, terofenamate and tolfenamic acid; arylacetic acid derivatives such as acemetacin, alclofenac, amfenac, bufexamac, cinmetacin, clopirac, diclofenac sodium, etodolac, felbinac, fenclofenac, fenclorac, fenclozic acid, fentiazac, glucametacin, ibufenac, indomethacin, isofezolac, isoxepac, lonazolac, metiazinic acid, oxametacine, proglumetacin, sulindac, tiaramide, tolmetin and zomepirac; arylbutyric acid derivatives such as bumadizon, butibufen, fenbufen and xenbucin; arylcarboxylic acids such as clidanac, ketorolac and tinoridine; arylpropionic acid derivatives such as alminoprofen, benoxaprofen, bucloxic acid, carprofen, fenoprofen, flunoxaprofen, flurbiprofen, ibuprofen, ibuproxam, indoprofen, ketoprofen, loxoprofen, miroprofen, naproxen, oxaprozin, piketoprofen, pirprofen, pranoprofen, protizinic acid, suprofen and tiaprofenic acid; pyrazoles such as difenamizole and epirizole; pyrazolones such as apazone, benzpiperylon, feprazone, mofebutazone, morazone, oxyphenbutazone, phenybutazone, pipebuzone, propyphenazone, ramifenazone, suxibuzone and thiazolinobutazone; salicylic acid derivatives such as acetaminosalol, aspirin, benorylate, bromosaligenin, calcium acetylsalicylate, diflunisal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamine o-acetic acid, salicylsulfuric acid, salsalate and sulfasalazine; thiazinecarboxamides such as droxicam, isoxicam, piroxicam and tenoxicam; others such as ε-acetamidocaproic acid, s-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole and tenidap; and pharmaceutically acceptable salts thereof.

Examples of steroidal anti-inflammatory agents (glucocorticoids) include 21-acetoxyprefnenolone, aalclometasone, algestone, amicinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumehtasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol priopionate, halometasone, halopredone acetate, hydrocortamate, hydrocortisone, loteprednol etabonate, mazipredone, medrysone, meprednisone, methyolprednisolone, mometasone furoate, paramethasone, prednicarbate, prednisolone, prednisolone 25-diethylaminoacetate, prednisone sodium phosphate, prednisone, prednival, prednylidene, rimexolone, tixocortal, triamcinolone, triamcinolone acetonide, triamcinolone benetonide, triamcinolone hexacetonide, and pharmaceutically acceptable salts thereof.

Analgesic agents include narcotic and non-narcotic analgesics. Narcotic analgesic agents include alfentanil, allylprodine, alphaprodine, anileridine, benzylmorphine, bezitramide, buprenorphine, butorphanol, clonitazene, codeine, codeine methyl bromide, codeine phosphate, codeine sulfate, desomorphine, dextromoramide, dezocine, diampromide, dihydrocodeine, dihydrocodeinone enol acetate, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, hydrocodone, hydromorphone, hydroxypethidine, isomethadone, ketobemidone, levorphanol, lofentanil, meperidine, meptazinol, metazocine, methadone hydrochloride, metopon, morphine, myrophine, nalbuphine, narceine, nicomorphine, norlevorphanol, normethadone, normorphine, norpipanone, opium, oxycodone, oxymorphone, papaveretum, pentazocine, phenadoxone, phenazocine, pheoperidine, piminodine, piritramide, proheptazine, promedol, properidine, propiram, propoxyphene, rumifentanil, sufentanil, tilidine, and pharmaceutically acceptable salts thereof.

Non-narcotic analgesics include aceclofenac, acetaminophen, acetaminosalol, acetanilide, acetylsalicylsalicylic acid, alclofenac, alminoprofen, aloxiprin, aluminum bis(acetylsalicylate), aminochlorthenoxazin, 2-amino-4-picoline, aminopropylon, aminopyrine, ammonium salicylate, amtolmetin guacil, antipyrine, antipyrine salicylate, antrafenine, apazone, aspirin, benorylate, benoxaprofen, benzpiperylon, benzydamine, bermoprofen, brofenac, p-bromoacetanilide, 5-bromosalicylic acid acetate, bucetin, bufexamac, bumadizon, butacetin, calcium acetylsalicylate, carbamazepine, carbiphene, carsalam, chloralantipyrine, chlorthenoxazin(e), choline salicylate, cinchophen, ciramadol, clometacin, cropropamide, crotethamide, dexoxadrol, difenamizole, diflunisal, dihydroxyaluminum acetylsalicylate, dipyrocetyl, dipyrone, emorfazone, enfenamic acid, epirizole, etersalate, ethenzamide, ethoxazene, etodolac, felbinac, fenoprofen, floctafenine, flufenamic acid, fluoresone, flupirtine, flupro-quazone, flurbiprofen, fosfosal, gentisic acid, glafenine, ibufenac, imidazole salicylate, indomethacin, indoprofen, isofezolac, isoladol, isonixin, ketoprofen, ketorolac, p-lactophenetide, lefetamine, loxoprofen, lysine acetylsalicylate, magnesium acetylsalicylate, methotrimeprazine, metofoline, miroprofen, morazone, morpholine salicylate, naproxen, nefopam, nifenazone, 5' nitro-2' propoxyacetanilide, parsalmide, perisoxal, phenacetin, phenazopyridine hydrochloride, phenocoll, phenopyrazone, phenyl acetylsalicylate, phenyl salicylate, phenyramidol, pipebuzone, piperylone, prodilidine, propacetamol, propyphenazone, proxazole, quinine salicylate, ramifenazone, rimazolium metilsulfate, salacetamide, salicin, salicylamide, salicylamide o-acetic acid, salicylsulfuric acid, salsalte, salverine, simetride, sodium salicylate, sulfamipyrine, suprofen, talniflumate, tenoxicam, terofenamate, tetradrine, tinoridine, tolfenamic acid, tolpronine, tramadol, viminol, xenbucin, zomepirac, and pharmaceutically acceptable salts thereof.

Local anesthetic agents include amucaine, amolanone, amylocaine hydrochloride, benoxinate, benzocaine, betoxycaine, biphenamine, bupivacaine, butacaine, butaben, butanilicaine, butethamine, butoxycaine, carticaine, chloroprocaine hydrochloride, cocaethylene, cocaine, cyclomethycaine, dibucaine hydrochloride, dimethisoquin, dimethocaine, diperadon hydrochloride, dyclonine, ecgonidine, ecgonine, ethyl chloride, beta-eucaine, euprocin, fenalcomine, fomocaine, hexylcaine hydrochloride, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octacaine, orthocaine, oxethazaine, parethoxycaine, phenacaine hydrochloride, phenol, piperocaine, piridocaine, polidocanol, pramoxine, prilocaine, procaine, propanocaine, proparacaine, propipocaine, propoxycaine hydrochloride, pseudococaine, pyrrocaine, ropavacaine, salicyl alcohol, tetracaine hydrochloride, tolycaine, trimecaine, zolamine, and pharmaceutically acceptable salts thereof.

Antispasmodic agents include alibendol, ambucetamide, aminopromazine, apoatropine, bevonium methyl sulfate, bietamiverine, butaverine, butropium bromide, n-butylscopolammonium bromide, caroverine, cimetropium bromide, cinnamedrine, clebopride, coniine hydrobromide, coniine hydrochloride, cyclonium iodide, difemerine, diisopromine, dioxaphetyl butyrate, diponium bromide, drofenine, emepronium bromide, ethaverine, feclemine, fenalamide, fenoverine, fenpiprane, fenpiverinium bromide, fentonium bromide, flavoxate, flopropione, gluconic acid, guaiactamine, hydramitrazine, hymecromone, leiopyrrole, mebeverine, moxaverine, nafiverine, octamylamine, octaverine, oxybutynin chloride, pentapiperide, phenamacide hydrochloride, phloroglucinol, pinaverium bromide, piperilate, pipoxolan hydrochloride, pramiverin, prifinium bromide, properidine, propivane, propyromazine, prozapine, racefemine, rociverine, spasmolytol, stilonium iodide, sultroponium, tiemonium iodide, tiquizium bromide, tiropramide, trepibutone, tricromyl, trifolium, trimebutine, n,n-1trimethyl-3,3-diphenylpropylamine, tropenzile, trospium chloride, xenytropium bromide, and pharmaceutically acceptable salts thereof.

Two particularly preferred therapeutic agents for the practice of the present invention are (a) ketorolac and pharmaceutically acceptable salts thereof (e.g., the tromethamine salt thereof, sold under the commercial name Toradol®) and (b) 4-diethylamino-2-butynylphenylcyclohexylglycolate and pharmaceutically acceptable salts thereof (e.g., 4-diethylamino-2-butynylphenylcyclohexylglycolate hydrochloride, also known as oxybutynin chloride, sold under the commercial name Ditropan®).

Once disposed within the body of the patient, the therapeutic agent is released from the medical device. The dose rate my vary depending on the application and the size of the patient. An acceptable dose rate of a therapeutic agent from the medical device is about 0.01 mg/day to about 100 mg/day, and preferably about 0.2 mg/day to about 20 mg/day. In a particularly preferred embodiment, the dose rate of a therapeutic agent from the medical device is about 1 mg/day to about 5 mg/day.

The dimensions of the various medical devices 100, 300, 500 may vary depending on the application and the size of the patient. For example, referring to FIG. 1, an acceptable range for the outside diameter 150 of the elongated member 110 is about 4 French to about 9 French, and preferably about 4.8 French to about 7.3 French. When a larger outside diameter 150 is required, such as, for example, when a high flow volume or a greater stiffness is desired, an elongated member 110 having a larger outside diameter 150 may be used. An acceptable larger outside diameter 150 of the elongated member 110 may be about 8 French to about 12 French. The length of the elongated member 110 may also vary to suit a particular application, for example, the size of the patient and the particular bodily lumen that the device will be placed in.

In operation, the medical device 100, 300, 500 of the present invention is loaded with one or more therapeutic agents and inserted into the body of a patient. Once positioned in a desired location, the medical device maintains an open passageway for passing bodily fluids and releases one or more therapeutic agents into the patient's body. Returning to FIG. 1, the therapeutic agent 108 may be released into the patient by diffusing through the walls 104 of the elongated member 110. The therapeutic agent 108 diffuses into the patient's body most efficiently when the agent 108 is in a liquid state. Where the therapeutic agent 108 is a solid, however, bodily fluids must first diffuse into the enclosed internal space 101 through the walls 104 and dissolve the therapeutic agent 108 contained therein. Once at least some of the agent 108 has dissolved, it may then diffuse out of the enclosed internal space 101 and into the patient's body.

The rate of release of the therapeutic agent is dependent on the mechanism by which the agent is delivered to the patient. Returning to FIG. 3, release of an agent may occur by diffusing through the elongated body 310 and/or by passing through the pores 304, 306, 314, 316. The dose-rate is maximized where the therapeutic agent is delivered by both mechanisms simultaneously. In an alternative embodiment, the stent 300 is constructed from a hydrophobic polymer and prevents a hydrophilic agent from diffusing through the elongated member 310. As a result, the therapeutic agent is released into the patient's body only through the pores 304, 306, 314, 316. Moreover, a diameter 375 of the pores 304, 306, 314, 316 may be varied to control the flow therethrough with or without the use of a plug. In an alternative embodiment, a first region 330 is constructed from a hydrophilic polymer and a second region 340 is constructed from a hydrophobic polymer, thus allowing a hydrophilic agent to diffuse through only a portion of the stent 300.

The various embodiments of the medical device 100, 300, 500 allow a medical professional to localize the release of the therapeutic agent to a particular area of the patient's body. As shown in FIG. 3, the enclosed internal spaces 301, 311 are generally located in the first region 330 and the second region 340, respectively. Thus, the therapeutic agent is released to tissue generally surrounding the first region 330 and the second region 340. In a particular embodiment, diffusion through the elongated member 310 is prevented, thus focusing delivery of the therapeutic agent to tissue closest to the pores 304, 306, 314, 316. In another embodiment, the enclosed internal spaces 301, 311 contain different therapeutic agents. As such, the medical professional can customize treatment for different tissues in the patient's body based on the positions of the first region 330 and second region 340 (See FIG. 7).

The stent 500 shown in FIG. 5 also allows a medical professional to control the location, time, and rate of release similar to the stent 300 of FIG. 3. The arrangement of the enclosed internal spaces 501, 511 allows the stent 500 to deliver the therapeutic agent on opposing sides of the longitudinal axis 588 of the elongated member 510. Because the enclosed internal spaces 511, 501 extend substantially along the entire longitudinal axis 588 of the elongated member 510, diffusion of an agent through the elongated member 510 may occur over substantially the entire length of the elongated member 510. Where the elongated member 510 is constructed from a hydrophobic polymer, however, a hydrophilic agent may only be delivered to a patient's body through the pores 504, 506, 514, 516, thus localizing treatment to tissue closest to the first region 570 and the second region 590. In an alternative embodiment, a plurality of pores may be defined along substantially the entire length of the elongated member 510 and in fluid communication with the first enclosed internal space 501 and/or the second enclosed internal space 511.

Figure 7:
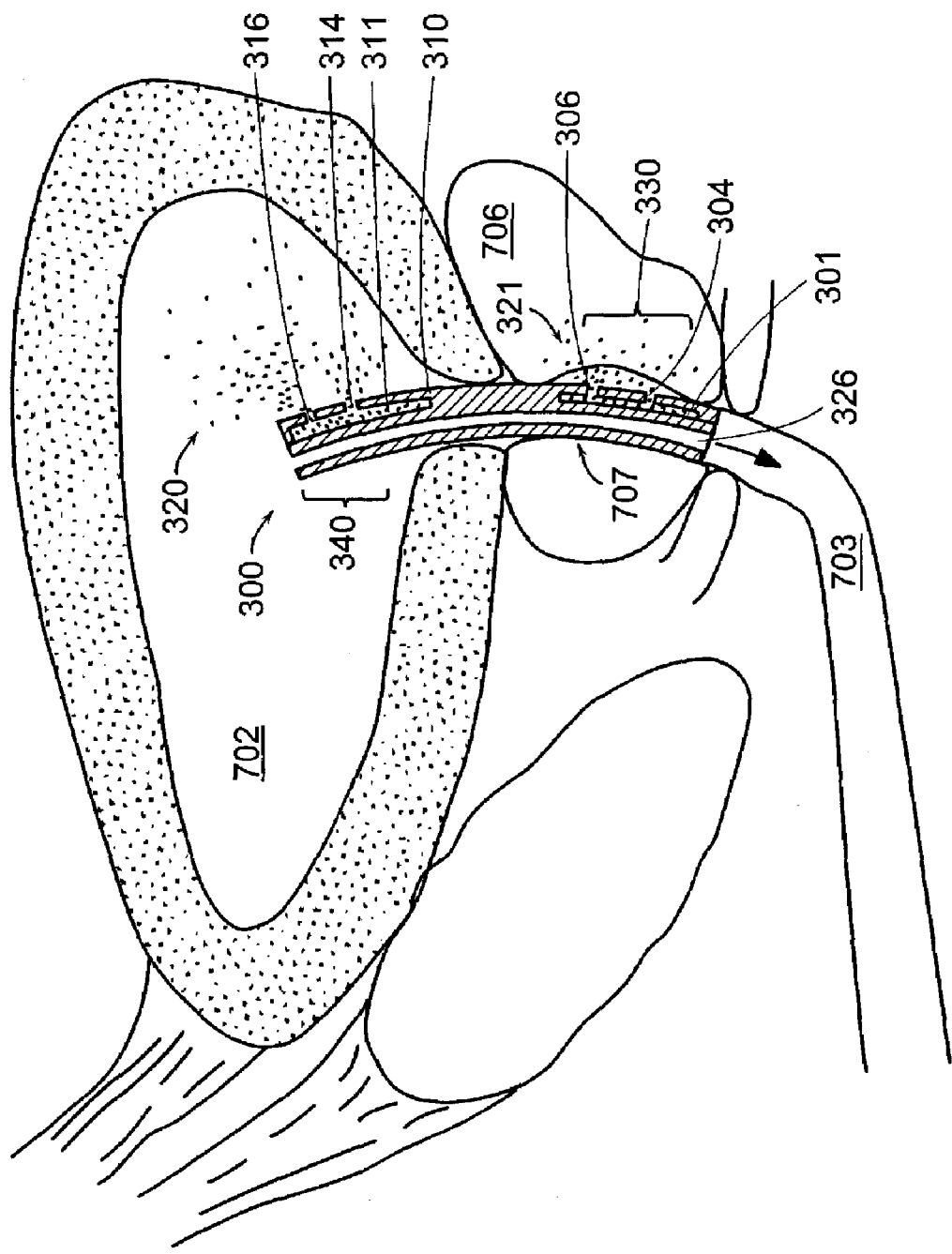
FIG. 7 illustrates the stent of FIG. 3 placed in the prostatic urethra of a patient's body.

FIG. 7 depicts the stent 300 of FIG. 3 inserted into a prostatic urethra 707 of a patient, thereby maintaining an open passageway therethrough. The elongated member 310 is positioned such that the first region 330 is adjacent to the patient's prostate 706 and the second region 340 is within the patient's bladder 702. The stent 300 allows the medical professional to simultaneously treat the prostate 706 and the bladder 702 with different therapeutic agents 320, 321. In operation, the first enclosed internal space 301 delivers the first therapeutic agent 321 to the prostate 706 through pores 304, 306. Additionally, the second enclosed internal space 311 delivers the second therapeutic agent 320 into the bladder 702 through pores 314, 316. The passage 326 passes urine from the bladder 702 into the urethra 703.

The methods for inserting the medical device vary according to the particular application for which the device is employed. Where the medical device is used as a prostatic stent (shown in FIG. 7), for example, a medical professional or physician inserts the first end of the stent into the patient's meatus. To advance the stent into the urethra, the physician uses a pusher or stylet that includes a shoulder portion for abutting the second end of the stent. The shoulder portion provides leverage and support for advancing the stent through the patient's urinary tract. To couple the stylet to the stent, the physician inserts the pusher into at least a portion of the stent's passage via the opening at the second end. Accordingly, the outer diameter of the stylet must be smaller than the diameter of the passage. Next, the physician advances the stylet through the passage until the stylet's shoulder portion abuts the second end of the stent. The stylet should be long enough such that a portion thereof remains outside the patient's body when the stent is properly positioned within the urinary system of the patient. By applying force to the stylet, the physician advances both the stylet and the prostatic stent through the urethra until the first end of the stent is located substantially within the bladder and the second end is proximal to the external sphincter (See FIG. 7). The physician can monitor the location of the stent using radiographic techniques. Once the stent is properly positioned, the stylet is retracted from the patient's body.

To protect the patient's urethra from irritation, the medical professional may insert the stent into a sheath prior to inserting the stent into the patient's body. The sheath is a smooth tubular member sized to receive the prostatic stent. The leading portion of the sheath can include a tapered tip, which facilitates passage through a bodily lumen. A retraction device can be coupled to the sheath for removing the sheath from the patient after the stent is inserted into the patient. The retraction device can be a thread-like structure that is disposed in the urethra and extends outside of the patient while a medical professional inserts the stent into the patient's body. Once the stent is properly positioned in the patient's body, the physician removes the sheath by drawing the retraction device out of the body. The drawing action causes the stent to slip through an opening in the tip of the sheath and remain positioned in the desired location. When drawing the sheath retraction structure out of the body, a sufficient amount of counter-force should be applied to the stylet to maintain the proper position of the stent. After the sheath is removed from the patient, the stylet may be retrieved from the patient's body. It is contemplated that the medical device of the present invention can be inserted into the body of a patient for a particular application using methods known to those skilled in the art.

Having thus described certain embodiments of the present invention, various alterations, modifications, and improvements will be apparent to those of ordinary skill. Such alterations, modifications, and improvements are intended to be within the spirit and scope of the invention. Accordingly, the foregoing description of embodiments of the invention is not intended to be limiting.

What is claimed is:

1. A stent for passing one or more bodily fluids and releasing at least one therapeutic agent into a body of a patient, the device comprising:
    an elongated member defining a passage for passing the one or more bodily fluids, the passage extending at least partially through the elongated member; and
    an enclosed internal space defined as a reservoir within the elongated member which has been loaded with at least one therapeutic agent so that said therapeutic agent is disposed therein prior to when the stent is disposed within the body of the patient and is releasable into the body of the patient through the elongated member when the stent is disposed within the body of the patient, wherein the enclosed internal space extends at least partially along the length of the elongated member and is coincident with a longitudinal axis of the passage; and at least one sealed opening defined by one end of the elongated member, the opening in communication with the enclosed internal space to provide access to the enclosed internal space for loading the at least one therapeutic agent prior to use.

2. The stent of claim 1 wherein the elongated member defines at least one pore in communication with the enclosed internal space for releasing the at least one therapeutic agent into the body of a patient when the medical device is disposed within the body of the patient.

3. The stent of claim 2 further comprising at least one plug disposed within the at least one pore, wherein the at least one plug comprises a biodegradable barrier.

4. The stent of claim 2 wherein the elongated member comprises a hydrophobic polymer.

5. The stent of claim 1 wherein the enclosed internal space extends along substantially the entire length of the elongated member.

6. The stent of claim 1 wherein the passage is eccentric to the elongated member.

7. The stent of claim 6 wherein the enclosed internal space extends along a length of the elongated member substantially parallel to the passage.

8. The stent of claim 7 wherein the enclosed internal space is eccentric to the elongated member.

9. The stent claim 1 further comprising a biodegradable coating disposed on an external surface of the elongated member.

10. The medical device of claim 9 wherein the biodegradable coating includes at least one therapeutic agent.

11. The stent of claim 1 wherein the elongated member comprises:
a first polymer having a first durometer value; and
a second polymer having a second durometer value.

12. The stent of claim 1 further comprising a second enclosed internal space defined by the elongated member for holding a second therapeutic agent.

13. The stent device of claim 12 wherein the enclosed internal space and second enclosed internal space are disposed on opposing sides of the passage along the longitudinal axis of the elongated member.

14. The medical device of claim 12 further comprising a second therapeutic agent placeable within at least a portion of the second enclosed internal space and releasable into the body of the patient through the elongated member when the medical device is disposed within the body of the patient.

15. The stent of claim 14 wherein the at least one therapeutic agent and the second therapeutic agent are the same.

16. The stent of claim 14 wherein at least one of the enclosed internal space and second enclosed internal space includes a plurality of therapeutic agents.

17. The stent of claim 12 wherein the elongated member defines at least one pore in communication with the second enclosed internal space for releasing the second therapeutic agent into the body of a patient when the medical device is disposed within the body of the patient.

18. The stent of claim 17 further comprising at least one plug disposed within the at least one pore, wherein the at least one plug comprises a biodegradable barrier.

19. The medical device of claim 1 wherein the opening is sealed with a radiopaque material.

20. A method of placing a stent for passing one or more bodily fluids and releasing at least one therapeutic agent into a body of a patient, comprising:
(a) providing a stent comprising:
(i) an elongated member defining a passage for passing the one or more bodily fluids, the passage extending at least partially through the elongated member;
(ii) an enclosed internal space defined as a reservoir within the elongated member which has been pre-loaded with the at least one therapeutic agent so that said therapeutic agent is disposed therein prior to when the stent is disposed within the body of the patient and is releasable into the body of the patient through the elongated member when the stern is disposed within the body of the patient, wherein the enclosed internal space extends at least partially along the length of the elongated member and is coincident with a longitudinal axis of the passage; and at least one sealed opening defined by one end of the elongated member, the opening in communication with the enclosed internal space to provide access to the enclosed internal space for loading the at least one therapeutic agent prior to use; and
(b) placing the stent into the body of the patient.

21. The method of claim 20 wherein the opening is sealed with a radiopaque material.

22. The method of claim 21 wherein the placing step comprises viewing the radiopaque material through a fluoroscope.

23. A method for delivering at least one therapeutic agent into a body of a patient, comprising:
(a) providing a stent comprising:
(i) an elongated member defining a passage for passing the one or more bodily fluids, the passage extending at least partially through the elongated member;
(ii) an enclosed internal space defined as a reservoir within the elongated member for holding the at least one therapeutic agent; and
(iii) at least one therapeutic agent loaded within at least a portion of the enclosed internal space so that said therapeutic agent is disposed therein prior to when the stent is disposed within the body of the patient and releasable into the body of the patient through the elongated member when the stent is disposed within the body of the patient wherein at least one sealed opening is defined by one end of the elongated member, the opening in communication with the enclosed internal space to provide access to the enclosed internal snace for loading the at least one therapeutic agent prior to use; and
(b) placing the stern into the body of the patient; and
(c) passing the at least one therapeutic agent through the elongated member, thereby delivering the therapeutic agent to the body of the patient.

24. The method of claim 23 wherein the placing step comprises inserting the stent within at least one of a urethra and a ureter.

25. The method of claim 23 wherein the at least one therapeutic agent is passed through the elongated member by at least one of diffusion and dissolution.

26. The method of claim 23 wherein the elongated member defines at least one pore in communication with the enclosed internal space for releasing the at least one therapeutic agent into the body of a patient when the stent is disposed within the body of the patient.

27. The method of claim 26 wherein the passing step comprises passing the at least one therapeutic agent through the at least one pore.

28. The method of claim 26 further comprising at least one plug disposed within the at least one pore, wherein the at least one plug comprises a biodegradable barrier.

29. The method of claim 28 wherein the passing step comprises:
degrading the biodegradable barrier; and
passing the at least one therapeutic agent through the at least one pore.

30. The method of claim 26 wherein the elongated member comprises a hydrophobic polymer.

31. The method of claim 23 wherein the stent comprises a biodegradable coating disposed on an external surface of the elongated member.

32. The method of claim 31 wherein the biodegradable coating comprises a therapeutic agent.

33. The method of claim 32 wherein the passing step comprise releasing the therapeutic agent by degrading the biodegradable coating into the body of the patient.

34. The stent of claim 1, wherein the one or more therapeutic agents are selected from the group consisting of anti-inflammatory agents, analgesic agents, antispasmodic agents and combinations thereof.

35. The method of claim 20, wherein the one or more therapeutic agents are selected from the group consisting of anti-inflammatozy agents, analgesic agents, antispasmodic agents and combinations thereof.

36. The method of claim 23, wherein the one or more therapeutic agents are selected from the group consisting of anti-inflammatory agents, analgesic agents, antispasmodic agents and combinations thereof.

37. The stent of claim 1, wherein at least one of the therapeutic agents comprises ketorolac, pharmaceutically acceptable salts of ketorolac, 4-diethylamino-2-buthynylphenylcyclohexylglycolate, or pharmaceutically acceptable salts of 4-diethylamino-2-buthynylphenylcyclohexylglycolate.

38. The method of claim 20, wherein at least one of the therapeutic agents comprises ketorolac, pharmaceutically acceptable salts of ketorolac, 4-diethylamino-2-buthynylphenylcyclohexylglycolate, or pharmaceutically acceptable salts of 4-diethylamino-2-buthynylphenylcyclohexylglycolate.

39. The method of claim 23, wherein at least one of the one or more therapeutic agents comprises ketorolac, pharmaceutically acceptable salts of ketorolac, 4-diethylamino-2-buthynylphenylcycohexyglycolate, or pharmaceutically acceptable salts of 4-diethylamino-2-buthynylphenylcyclohexylglycolate.

40. A method of placing a stent for passing one or more bodily fluids and releasing at least one therapeutic agent into a body of a patient, comprising:
(a) providing a stent comprising:
  (i) an elongated member defining a passage for passing the one or more bodily fluids, the passage extending at least partially through the elongated member: and
  (ii) an enclosed internal space defined as a reservoir within the elongated member which has been pre-loaded with the at least one therapeutic agent so that said therapeutic agent is disposed therein prior to when the stent is disposed within the body of the patient and is releasable into the body of the patient through the elongated member when the stent is disnosed within the body of the patient, wherein the enclosed internal space extends at least partially along the length of the elongated member and is coincident with a longitudinal axis of the passage; and
(b) placing the stent into the body of the patient, wherein the elongated member also defines an opening at one end of the elongated member, the opening in communication with the enclosed internal space to provide access to the enclosed internal space for loading the at least one therapeutic agent, the opening for being sealed after loading and prior to the medical device being disposed within the body of the patient.

41. The method of claim 20, wherein the elongated member also defines an opening at one end of the elongated member, the opening in communication with the enclosed internal space to provide access to the enclosed internal space for loading the at least one therapeutic agent, the opening for being sealed after loading and prior to the medical device being disposed within the body of the patient.

* * * * *

UNITED STATES PATENT AND TRADEMARK OFFICE
CERTIFICATE OF CORRECTION

PATENT NO. : 7,288,084 B2
APPLICATION NO. : 10/424621
DATED : October 30, 2007
INVENTOR(S) : Jianmin Li Page 1 of 2

It is certified that error appears in the above-identified patent and that said Letters Patent is hereby corrected as shown below:

Col. 1, line 39, after "the invention", add --,--.

Col. 1, line 64, change first word "drug-release" to --drug release--.

Col. 8, line 4, after "is", delete "a".

Col. 8, line 10, after "space", change "31 1", to --311--.

Col. 11, line 25, after "is", delete "a".

Col. 14, line 28, after first word "rate", change "my" to --may--.

Claim 10, Col. 17, line 38, after first word "The", change "medical device" to --stent--.

Claim 13, Col. 17, line 47, after "stent", delete --device--.

Claim 14, Col. 17, line 51, after first word "The", change "medical device" to --stent--.

Claim 19, Col. 18, line 4, after first word "The", change "medical device" to --stent--.

Claim 20, Col. 18, line 19, after "when the", change "stern" to --stent--.

Claim 23, Col. 18, line 54, after "internal", change "snace" to --space--.

Claim 23, Col. 18, line 56, after first words "(b) placing the", change "stern" to --stent--.

Claim 33, Col. 19, line 23, change first word "comprise" to --comprises--.

UNITED STATES PATENT AND TRADEMARK OFFICE
CERTIFICATE OF CORRECTION

PATENT NO. : 7,288,084 B2
APPLICATION NO. : 10/424621
DATED : October 30, 2007
INVENTOR(S) : Jianmin Li It is certified that error appears in the above-identified patent and that said Letters Patent is hereby corrected as shown below:

Claim 35, Col. 19, line 31, change first word "anti-inflammatozy" to --anti-inflammatory--.

Claim 40, Col. 20, line 24, change first word "disnosed", to --disposed--.

Claim 40, Col. 20, line 36, after "the", change "medical device" to --stent--.

Claim 41, Col. 20, line 44, change first words "medical device" to --stent--.

Signed and Sealed this

Second Day of September, 2008

JON W. DUDAS
*Director of the United States Patent and Trademark Office*